United States Patent [19]

Heimlich

[11] 4,350,167

[45] Sep. 21, 1982

[54] RESPIRATORY EXERCISER

[76] Inventor: Henry J. Heimlich, 17 Elmhurst Pl., Cincinnati, Ohio 45208

[21] Appl. No.: 148,510

[22] Filed: May 9, 1980

[51] Int. Cl.³ .............................................. A61B 5/08
[52] U.S. Cl. .................................... 128/727; 73/262; 92/92; 128/728
[58] Field of Search ................... 128/205.23, 716, 719, 128/720, 725, 727, 728, 730, 774, 777, 205.17; 73/262; 92/92 R

[56] References Cited

U.S. PATENT DOCUMENTS

| | | | |
|---|---|---|---|
| 3,722,506 | 3/1973 | McMillan, Jr. | 128/727 |
| 3,895,533 | 7/1975 | Steier | 128/774 |
| 3,898,878 | 8/1975 | Elam | 128/205.23 |
| 4,096,855 | 6/1978 | Fleury, Jr. | 128/727 |
| 4,233,990 | 11/1980 | Yardley | 128/728 |

Primary Examiner—Henry J. Recla
Attorney, Agent, or Firm—Frost & Jacobs

[57] ABSTRACT

A respiratory exercise device for measuring the volume of air inhaled by the user, the device comprising an essentially rigid transparent container having an inhalation tube by means of which air is evacuated from the container, the container having an expansible member in communication with the outside air which expands within the container as the air in the container is evacuated, calibrated indicia being provided which measures the extent to which the expansible member is expanded, thereby indicating the volume of air withdrawn from the container.

4 Claims, 6 Drawing Figures

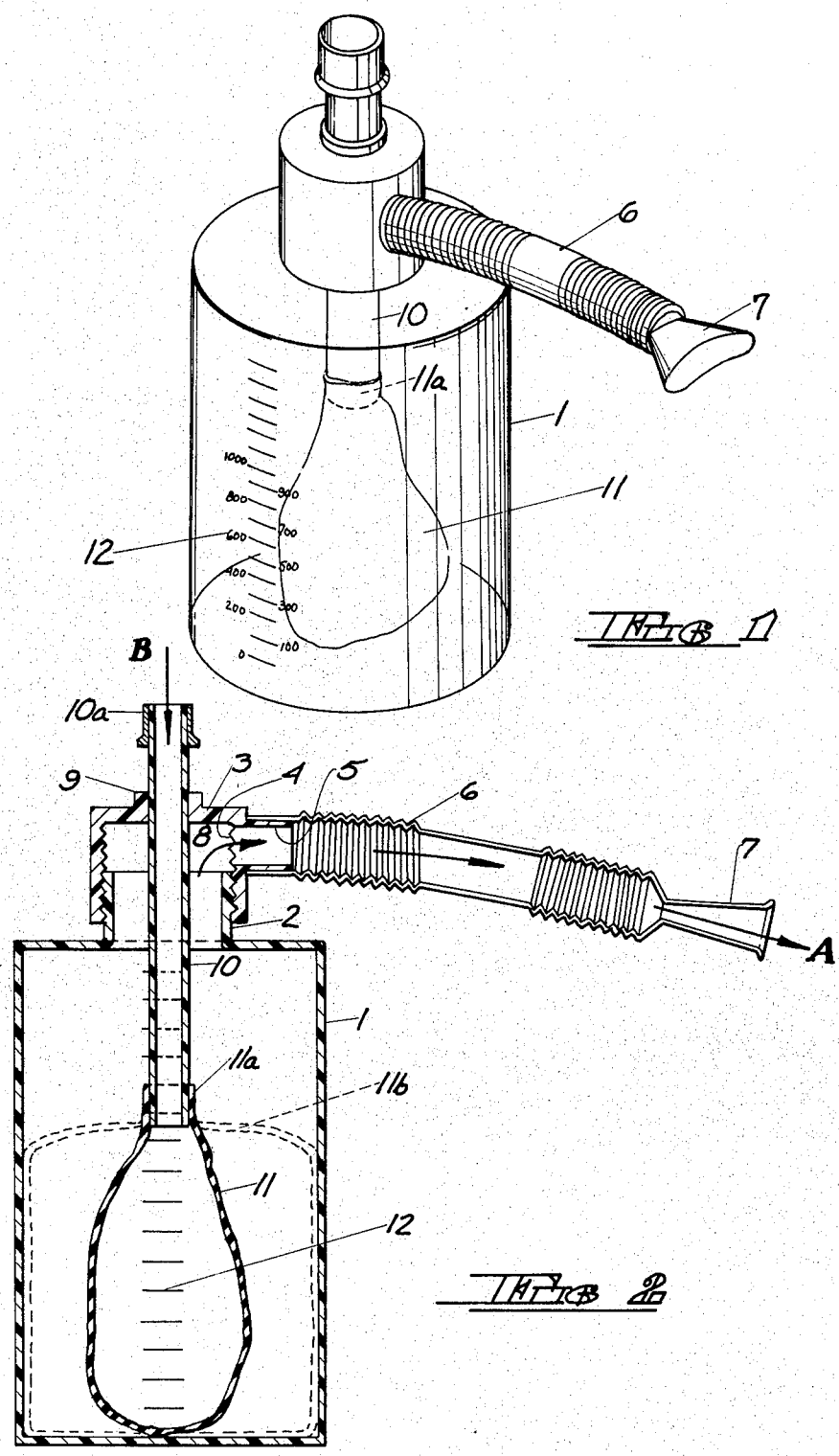

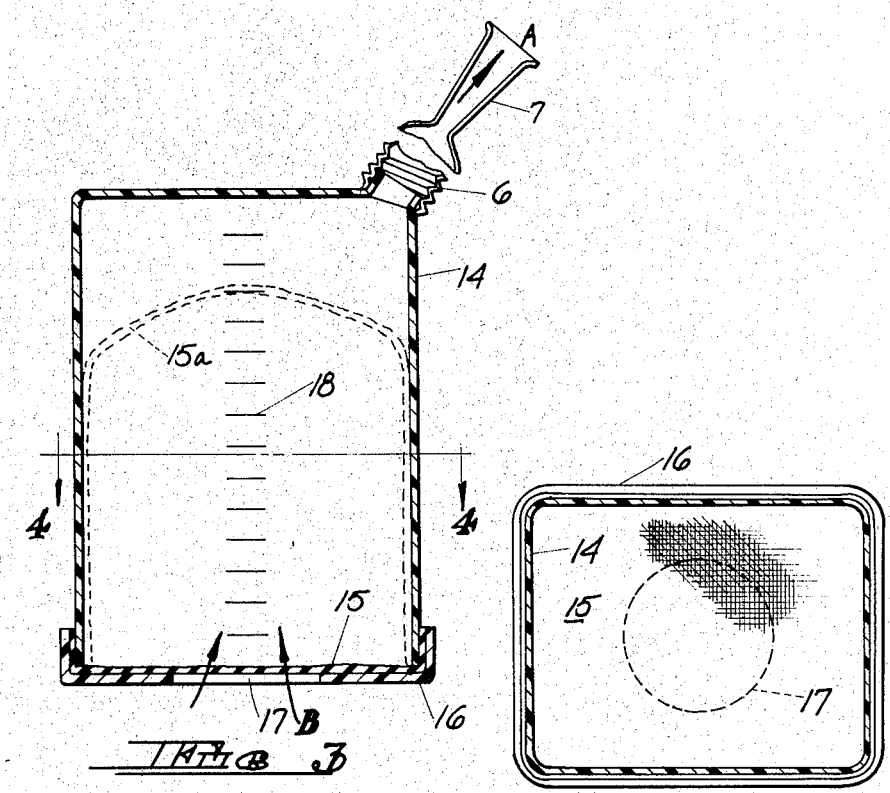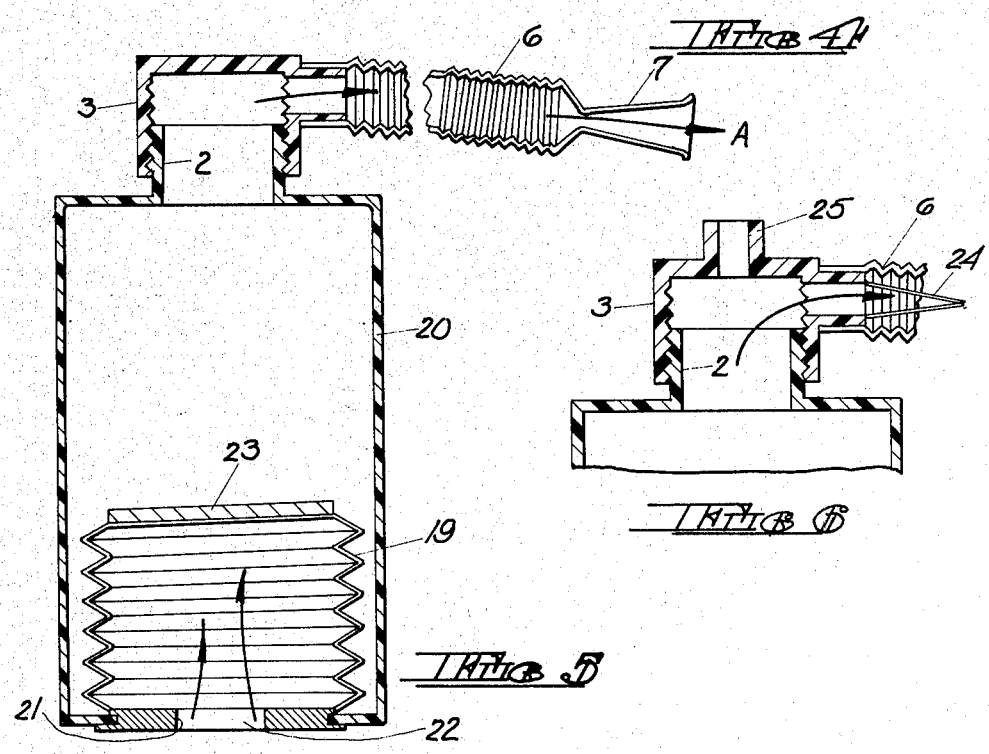

RESPIRATORY EXERCISER

This invention relates to a respiratory exercising device and more particularly to a deep-breathing exerciser which induces the user to hyperinflate his lungs.

BACKGROUND OF THE INVENTION

It has been found through scientific studies that expansion of the lungs through inspiration is extremely important in overcoming post-operative pneumonia and atalectasis. There are a number of devices currently available for single patient use which are intended to expand the user's lungs. They are generally referred to as incentive spirometers or incentive deep-breathing exercises. One such device is taught in U.S. Pat. No. 4,037,836 and another in U.S. Pat. No. 4,060,074. These devices comprise one or more vertically disposed chambers, the chambers each containing a lightweight ball, such as a ping pong ball, which is caused to rise as the user inhales through a flexible inhalation tube connected to the chambers. In another form of such device, a lightweight piston is fitted in a chamber in a manner such that withdrawal of the air from the chamber causes upward movement of the piston. Devices of this character measure the rate of air flow, i.e., air flow per second, to give an indication of what the patient is accomplishing in terms of lung expansion.

Researchers have determined that the rate of air flow is not the most satisfactory criteria for determining expansion of the lungs. One can achieve a very rapid air flow by inhaling suddenly, yet not adequately expand the lungs. Consequently the accepted recommendation is that the patient must slowly expand his lung volume, the volume of inhaled air and hence the extent to which the lungs have been expanded being the criteria for determining the effectiveness of the exercise. It is therefore desirable to provide a device which will encourage optimum lung expansion and provide a visual measurement of the volume of air inhaled, thereby providing an accurate indication of the extent to which the lungs have been expanded.

BRIEF SUMMARY OF THE INVENTION

The present invention is designed to meet the recommendation that the patient must slowly expand his lung volume, and this is accomplished by providing a device which measures the volume of inhaled air. To this end, a transparent container is provided, the container having a flexible inhalation tube by means of which the patient may withdraw air from the container. During use the container is effectively sealed from the outside air so that only the air contained within the container is withdrawn by the user. Since outside air at atmospheric pressure will enter the container through the inhalation tube, the air within the container will be at atmospheric pressure at the start of the exercise.

In order to measure the volume of air withdrawn from the container, an expansible member is arranged to expand within the container as the contained air is evacuated. The expansible member is in communication with the outside air, so that as the air within the container is evacuated by the user, thereby developing a negative pressure within the container, the expansible structure, being under atmospheric pressure, will expand within the container and in so doing will give an accurate indication of the volume of air which has been displaced and hence has been inhaled. By providing calibrated indicia on the container or on the expansible member, a visual indication will be given of the volume of air inhaled. At the end of inhalation, the expansible member may be maintained in the expanded condition by temporarily closing the orifice through which the expansible member communicates with the outside air, thereby affording the user ample time to accurately determine the volume of air which has been inhaled.

While primarily intended for post-operative use, the invention can be used by singers and athletes or any other individual interested in improving his respiratory expansion. The device will enhance proper breathing and increase expansion of the chest and hence better air exchange. The device also will be useful to persons suffering from emphysema.

BRIEF DESCRIPTION OF THE DRAWINGS

FIG. 1 is a perspective view of a respiratory exerciser in accordance with the invention.

FIG. 2 is a vertical sectional view of the exerciser shown in FIG. 1.

FIG. 3 is a vertical sectional view of a modification of the invention.

FIG. 4 is a sectional view taken along the line 4—4 of FIG. 3.

FIG. 5 is a vertical sectional view of another modification of the invention.

FIG. 6 is a fragmentary sectional view illustrating the use of a valve member in the inhalation tube.

DETAILED DESCRIPTION

Referring first to FIGS. 1 and 2, the exerciser comprises a container 1 preferably formed from a transparent plastic material. The container will be essentially rigid in the sense that it will maintain its shape when the air is evacuated from it. The shape of the container does not constitute a limitation on the invention and may vary depending upon the configuration of the expansible member, the primary objective being to cause the expansible member to expand within the container. The expansible member may be configured to conform to the shape of the container, although other configurations may be used. For example, if the expansible member is of special configuration and the container rectangular or cylindrical, the calibrated indicia may be in the form of a bulls-eye which will indicate the volume of air which has been displaced. In the embodiment illustrated, the container is cylindrical and has a threaded neck 2 at its upper end which receives a threaded cap 3, the cap projecting upwardly beyond the upper edge of the neck 2. The cap has a first orifice 4 surrounded by a sleeve-like fitting 5 adapted to receive a flexible inhalation tube 6 having a mouthpiece 7. The cap has a second orifice 8 with an annular shoulder 9 which receives an elongated tube 10, the tube projecting downwardly within the container 1. At its lowermost end the tube 10 mounts an expansible member 11 in the form of an elastic balloon the neck 11a of which surrounds and is secured to the lowermost end of tube 10.

In using the exerciser, the patient inhales through the mouthpiece 7, thereby withdrawing air from the container 1, as indicated by the Arrow A. Since the interior of the container is closed to outside air, a negative pressure will be developed in the container and the expansible member 11 will expand within the container, as indicated by the dotted lines 11b, such expansion being caused by outside air at atmospheric pressure entering the expansible member 11 through tube 10, as indicated by Arrow B. At the end of inhalation, by placing a finger or cap over the uppermost end 10a of the tube 10, the outside air drawn into the expansible member will be trapped and the member will remain expanded, thereby giving a sustained visual indication of the volume of air which has been inhaled, the volume of air inhaled having been displaced by an equal volume of air drawn into the expansible member.

The volume of inhaled air is measured by means of calibrated indicia 12 on one or more of the walls of the container 1 which enables the user to determine the extent to which the expansible member has been expanded and hence the volume of air contained within the expansible member, which is equal to the volume of air inhaled by the user. Preferably, the expansible member will be colored, i.e., red or blue, so that it will be easy to view and the extent of expansion can be readily determined. It is also preferred to mount the tube 10 for axial movement relative to the cap 3, thereby enabling the user to accurately position the expansible member relative to the container 1, depending upon the quantity of air the patient is capable of inhaling. While in the embodiment illustrated the container is provided with a threaded neck and cap for simiplicity and ease of assembly, it will be readily apparent that the inhalation tube could be connected directly to the container 1, the essential consideration being that the container is sealed against the ingress of outside air except for the tube 10 which permits outside air to enter the expansible member 11 as air is withdrawn from the container.

FIGS. 3 and 4 illustrate a modification of the invention wherein the expansible member is formed as a wall of the container. In the embodiment illustrated, the container 14 is rectangular in cross-section and has an open bottom closed by an expansible member 15 comprising an elastic membrane, such as rubber, secured to the marginal edges of the container body. The membrane may be covered by a protective cap 16 having an orifice 17 which exposes the membrane to the outside air.

In use, as the patient inhales and air is withdrawn from the container through inhalation tubes 6, the membrane 15 will expand within the container, as indicated by dotted lines 15a, due to the negative pressure created within the container which is replaced by outside air entering the container through orifice 17, the quantity of outside air entering the container to expand the membrane being equal to the quantity of air inhaled by the patient. Calibrated indicia 18 on one or more walls of the container provides an accurate indication of the volume of air inhaled by the patient. The expanded membrane 15 may be retained in its expanded position by closing the orifice 17, as by covering it with the palm of the user's hand. While in the embodiment illustrated, the bottom of the container is effectively collapsible inwardly by means of the elastic membrane 15, it will be evident that the expansible member could replace one of the side walls of the container, the primary consideration being that the container will remain essentially rigid as the wall forming membrane expands.

FIG. 5 illustrates a further embodiment of the invention wherein the expansible member is in the form of a bellows 19 formed from a thin flexible plastic material or other material impervious to air, the bellows 19 being secured to the container 20 by means of an airtight fitting 21 received in the bottom wall of the container, the fitting having an orifice 22 to permit outside air to enter the bellows and expand it upwardly into the container as air is withdrawn from the interior of the container by the patient. In order to insure the collapse of the bellows following inhalation, the bellows is provided with a weight 23, such as a plastic plate, which will cause the bellows to collapse to its fully retracted position following expansion during inhalation.

FIG. 6 illustrates a further modification wherein a one-way valve, such as a flutter valve 24, is positioned to permit air to be withdrawn through inhalation tube 6, while preventing air from flowing inwardly into the container through the inhalation tube. In this instance the cap 3 is provided with an orifice 25 in the form of a stem in communication with the outside air which may be closed by a finger or a suitable cap during inhalation. With this arrangement, the negative pressure buildup in the container will be maintained as long as the orifice 25 remains closed and it is not necessary for the user to close the orifice which communicates with the expansible member, such as the orifice 22 of FIG. 5, to maintain the expansible member in the expanded condition. Thus, upon completion of the exercise, the user may remove the inhalation tube from his mouth and maintain the expansible member in its expanded condition until the indicia can be read simply by maintaining his finger on orifice 25. When orifice 25 is opened, outside air will reenter the container through orifice 25, thereby permitting the expansible member to collapse.

As should now be evident, the invention provides a simple yet effective respiratory exerciser which measures the volume of air inhaled by the user irrespective of the rate of inhalation. While the invention has been described in detail with particular reference to several preferred embodiments, it will be understood that variations and modifications can be made without departing from the spirit and purpose of the invention.

What is claimed is:

1. A respiratory exercising device comprising:
   an essentially rigid transparent container,
   a first orifice in communication with the interior of the container,
   an inhalation tube connected to said first orifice,
   a second orifice in said container in communication with the outside air,
   an expansible chamber consisting of an elastic member located within said container and connected to said second orifice to communicate said expansible chamber to the outside air, said elastic member being of a size to expand within the confines of the container to conform to the contiguous wall surfaces thereof upon evacuation of air from the container through said inhalation tube,
   calibrated indicia positioned on said container with respect to said elastic member for measuring the extent to which said elastic member is expanded into contact with the contiguous wall surfaces of the container, and
   means for adjusting the position of the elastic member within said container in accordance with the inhalation capacity of the user, whereby to directly measure the volume of air withdrawn from the container through said inhalation tube.

2. The respiratory exercising device claimed in claim 1 wherein the means for adjusting the position of the elastic member within said container comprises an elongated tube projecting inwardly into said container through said second orifice, said tube being axially movable relative to said second orifice, and wherein said elastic member is in communication with the inner end of said tube.

3. The respiratory exercising device claimed in claim 2 wherein said elastic member comprises a rubber balloon having a mouth, and wherein the mouth of said balloon surrounds and is secured to the inner end of said tube.

4. A respiratory exercising device comprising:
an essentially rigid transparent container having a neck at its upper end,
a cap in engagement with said neck, said cap having an annular wall and a top wall,
a first orifice in said cap in communication with the interior of the container, said first orifice being defined by a sleeve-like fitting projecting outwardly from the annular wall of said cap,
an inhalation tube connected to said fitting,
a second orifice formed in the top wall of said container in communication with the outside air, said second orifice being surrounded by an annular shoulder,
an elongated tube projecting inwardly into the container through said second orifice, said tube being slidably received within said annular shoulder,
an expansible chamber comprising an elastic member located within said container, said elastic member having a mouth secured to the inner end of said elongated tube to place said elastic member in communication with the outside air, said elastic member being of a size to fully expand within the confines of the container upon evacuation of air from the container through said inhalation tube, and
calibrated indicia positioned on said container with respect to said elastic member for measuring the extent to which said elastic member is expanded within the container, whereby to directly measure the volume of air withdrawn from the container through said inhalation tube.

* * * * *